(12) United States Patent
Etoh et al.

(10) Patent No.: US 10,345,274 B2
(45) Date of Patent: Jul. 9, 2019

(54) MATERIAL DIAGNOSTIC METHOD

(71) Applicants: NUCLEAR FUEL INDUSTRIES, LIMITED, Tokyo (JP); THE UNIVERSITY OF TOKYO, Tokyo (JP)

(72) Inventors: Junji Etoh, Sennan-gun (JP); Mitsuyuki Sagisaka, Sennan-gun (JP); Yoshihiro Isobe, Sennan-gun (JP); Taira Okita, Tokyo (JP)

(73) Assignees: NUCLEAR FUEL INDUSTRIES, LIMITED, Tokyo (JP); THE UNIVERSITY OF TOKYO, Tokyo (JP)

( * ) Notice: Subject to any disclaimer, the term of this patent is extended or adjusted under 35 U.S.C. 154(b) by 674 days.

(21) Appl. No.: 14/405,692

(22) PCT Filed: Jun. 7, 2013

(86) PCT No.: PCT/JP2013/065826
§ 371 (c)(1),
(2) Date: Dec. 4, 2014

(87) PCT Pub. No.: WO2013/183759
PCT Pub. Date: Dec. 12, 2013

(65) Prior Publication Data
US 2015/0168356 A1 Jun. 18, 2015

(30) Foreign Application Priority Data
Jun. 8, 2012 (JP) .................................. 2012-130828

(51) Int. Cl.
*G01N 29/07* (2006.01)
*G01N 29/11* (2006.01)
(Continued)

(52) U.S. Cl.
CPC .............. *G01N 29/36* (2013.01); *G01N 29/07* (2013.01); *G01N 29/11* (2013.01); *G01N 29/42* (2013.01);
(Continued)

(58) Field of Classification Search
CPC ........ G01N 29/07; G01N 29/11; G01N 29/42; G01N 29/36; G01N 29/46; G01N 2291/044; G01N 2291/0234; G01N 2291/0289
(Continued)

(56) References Cited

U.S. PATENT DOCUMENTS 6,370,956 B1 * 4/2002 Bewlay ................ C23C 14/546
204/298.03
6,393,916 B1 * 5/2002 Bewlay ................ G01B 21/08
356/503

(Continued)

FOREIGN PATENT DOCUMENTS

EP 2 006 676 A1 12/2008
JP H06-201659 A 7/1994
(Continued)

OTHER PUBLICATIONS

J. Eto et al., "Development of Quantitative Non-Destructive Inspection Method for Microstructures Under Irradiation Using Decommissioned Reactor Materials (2) An Theoretical Approach", 2012 Annual Meeting of the Atomic Energy Society of Japan, Mar. 2, 2012, p. 457.
(Continued)

*Primary Examiner* — Jacques M Saint Surin
(74) *Attorney, Agent, or Firm* — Birch, Stewart, Kolasch & Birch LLP

(57) ABSTRACT

Provided is a material diagnostic method capable measuring and diagnosing in a nondestructive manner the type, quan-
(Continued)

tity of occurrence, depth distribution, and the like of even very small microstructures of about several tens of μm or less with sufficiently good precision. A material diagnostic method for using ultrasonic waves in a nondestructive manner to diagnose microstructures generated in a material, wherein changes in the scattering of ultrasonic waves by crystal grains are captured from bottom face waves and backscattered waves to thereby quantify the amount of change in microstructures, using the fact that changes in the properties of crystal grains produced by microstructures affect the scattering of ultrasonic waves.

12 Claims, 12 Drawing Sheets

(51) Int. Cl.
G01N 29/42 (2006.01)
G01N 29/46 (2006.01)
G01N 29/36 (2006.01)

(52) U.S. Cl.
CPC ..... *G01N 29/46* (2013.01); *G01N 2291/0234* (2013.01); *G01N 2291/0289* (2013.01); *G01N 2291/044* (2013.01)

(58) Field of Classification Search
USPC .................................................. 73/600, 627
See application file for complete search history.

(56) References Cited

U.S. PATENT DOCUMENTS

| | | | | |
|---|---|---|---|---|
| 7,278,315 | B1* | 10/2007 | Klein | G01N 21/1702 73/598 |
| 2009/0056454 | A1* | 3/2009 | Turner | B61K 9/08 73/600 |
| 2012/0132005 | A1* | 5/2012 | Turner | B61K 9/10 73/597 |

FOREIGN PATENT DOCUMENTS

| | | |
|---|---|---|
| JP | 09-138222 A | 5/1997 |
| JP | 2002-174627 A | 6/2002 |
| JP | 2002-303608 A | 10/2002 |
| JP | 2003-294880 A | 10/2003 |
| JP | 2008-261765 A | 10/2008 |
| JP | 2009-281846 A | 12/2009 |
| WO | WO 2007/003058 A1 | 1/2007 |

OTHER PUBLICATIONS

M. Sagisaka et al., "Development of Integrity Evaluation Approach for Fast Reactor Structural Materials Using EBR-II Decommissioned Reactor Reflector Blocks (3) Development of Diagnosis Method for Irradiation . . . ", 2010 Fall Meeting of the Atomic Energy Society of Japan, Aug. 27, 2010, p. 307.

Written Opinion of the International Searching Authority for Application No. PCT/JP2013/065826, dated Dec. 8, 2014, along with an English translation.

Y. Isobe et al., "Inspection of Irradiation-Induced Microstructures by Ultrasonic Signals", 2011 Annual Meeting of the Atomic Energy Society of Japan, Mar. 11, 2011, p. 90.

Alex Vary "Material Property Characterization", Section 12; In: A. Birks, R. Green "Nondestructive Testing Handbook", 1991, Paul McIntire, USA, XP009190928, vol. 7, pp. 383-431.

Extended European Search Report issued in corresponding European Application No. 13800539.2 on Jul. 27, 2016.

Office Action issued in corresponding Japanese Application No. 2012-130828, dated Dec. 12, 2016, with a partial English translation.

Proceedings for Process Equipment Research Forum, organized by Japan Petroleum Institute, pp. 40-43, issued on Nov. 22, 2000.

* cited by examiner

MATERIAL DIAGNOSTIC METHOD

FIELD OF THE INVENTION

The present invention relates to a material diagnostic method of performing non-destructive diagnosis concerning the kind, the amount of occurrence, the depth distribution and the like of microstructures such as precipitates and voids in a steel material such as stainless steel caused by irradiation of radiation, thermal aging, plastic deformation, or the like.

BACKGROUND OF THE INVENTION

In the conventional art, as techniques of diagnosing a microstructure change concerning the above-mentioned precipitates, voids, and the like having occurred in the steel material such as stainless steel by means of quantifying the kind, the amount of occurrence, the depth distribution, and the like thereof, techniques have been adopted that employ an electron microscope, ultrasonic, or the like.

The method employing an electron microscope is a destructive technique in which a sample is cut out from the material and then observed by the electron microscope so that the amount of microstructures near the surface is quantified. Nevertheless, when the depth distribution of the microstructures is to be quantified, problems arise like a large number of samples need be cut out.

In contrast, the method employing ultrasonic is a non-destructive technique in which ultrasonic is projected onto a material so that microstructures having occurred in a material are quantified and thereby diagnosis is achieved. In this method, a large number of samples like in the method employing an electron microscope need not be cut out. Thus, this method is preferable.

FIG. 1 schematically shows outlines of the measurement method employing ultrasonic. As shown in FIG. 1, when ultrasonic indicated by a bold rightward arrow are projected into a material, by an ultrasonic transducer indicated by the smaller rectangle, a signal (bottom surface wave) reflected from the material bottom surface indicated by a bold leftward arrow and a signal (backscattered wave) reflected from the inside of the material indicated by a thin arrow can be acquired by the ultrasonic transducer and converted into an ultrasonic wave form.

At that time, when microstructures such as voids, dislocations, and precipitates are present in the material, reflection from the microstructures is generated and added to the backscattered wave so that the backscattered wave intensity increases. On the other hand, the bottom surface wave intensity varies. Thus, when such intensities can be measured, occurrence of the microstructures can be recognized.

In a case of microstructures of approximately several tens of μm or larger, the ultrasonic intensity reflected and scattered directly from the microstructures is sufficiently large. Thus, the amount of variation in the backscattered wave intensity is large and hence, even when a material diagnostic measurement method employing ultrasonic of the conventional art is used, the microstructures of the material can sufficiently be quantified.

Nevertheless, in a case of fine microstructures, specifically, microstructures of approximately several tens of μm or smaller, the amount of variation in the backscattered wave intensity is as small as approximately 1/1000 of the backscattered wave intensity in crystal grains. Thus, scattering by crystal grains becomes dominant. Accordingly, a change in the backscattered wave intensity associated with the occurrence of microstructures is difficult to be identified as a clear signal. Thus, in a material diagnostic measurement employing ultrasonic of the conventional art, a quantification of these fine microstructure defects has been difficult.

Further, when the microstructures have occurred, the depth distribution thereof also need be quantified. Thus, for example, a technique of quantifying also the depth distribution from the obtained ultrasonic data by using wavelet transformation or the like is tried (e.g., Patent Document 1). Nevertheless, owing to large errors, quantification has been difficult.

Thus, various techniques of quantifying fine microstructures by using ultrasonic have been proposed (e.g., Patent Documents 2 to 4).

PRIOR ART REFERENCES

Patent Documents

[Patent Document 1] JP2002-303608A
[Patent Document 2] JP2003-294880A
[Patent Document 3] JP2008-261765A
[Patent Document 4] JP2009-281846A

SUMMARY OF THE INVENTION

Problems to be Solved by the Invention

Nevertheless, these techniques basically evaluate ultrasonic scattered directly by microstructures and hence are not yet satisfactory for precision quantification of microstructures of approximately several tens of μm or smaller.

Thus, in view of the above-mentioned problems in the prior art, an object of the present invention is to provide a material diagnostic method in which even for fine microstructures of approximately several tens of μm or smaller, non-destructive quantification with satisfactory precision can be achieved concerning the kind, the amount of occurrence, the depth distribution, and the like thereof so that diagnosis can be achieved.

Means for Solving the Problem (1) In the course of intensive investigation for a solution for the above-mentioned problem, the present inventors have focused attention on a fact that when microstructures such as precipitates of carbide or the like, voids, dislocations, and phase transformation have occurred in a material, in association with a change in the ultrasonic signal intensity, a change occurs also in crystal-grain physical property values (such as the volume, the density, and the sonic speed).

That is, for example, when voids serving as microstructures have occurred in crystal grains, in association with the occurrence of voids, the volume of the crystal grain increases and hence the density decreases. Further, in association with the occurrence of voids, Young's modulus decreases and hence the sonic speed propagating the crystal grain decreases (see FIG. 2).

On the other hand, when microstructures occur, a change arises in the ultrasonic signal intensity. That is, for example, a signal waveform of a case without the occurrence of microstructures shown in FIG. 3(a) goes into a signal waveform whose backscattered wave intensity has increased as shown in FIG. 3(b).

In view of a situation that in the conventional art, diagnosis of microstructures has been performed based on a change in the backscattered wave intensity of ultrasonic reflected directly from the microstructures so that diagnosis of fine microstructures has been difficult, the present inventors have performed intensive investigation with focusing attention on the above-mentioned relation between a change in the crystal-grain physical property values and a change in the ultrasonic signal intensity.

From the result, it has been recognized that the occurrence of microstructures causes a change in the intensity of the bottom surface wave and the backscattered wave as described above and that then, as shown in FIG. 4, a change in the wave height or the frequency spectrum in the backscattered wave relates to the microstructure distribution in the depth direction and, on the other hand, a change in the sonic speed and a change in the wave height or the frequency spectrum in the bottom surface wave relate to a material property change value average in the depth direction. Here, the above-mentioned frequency spectrums of the bottom surface wave and the backscattered wave can be calculated by performing frequency conversion on the temporal change of the ultrasonic signal waveform. Further, in the above-mentioned description, on the basis of a fact that when bottom surface wave make a round trip through the inside of a material, the signal (see FIG. 1) is affected by microstructures in the material through which the ultrasonic have passed, the "material property change value average" indicates as an average of a change in the material property represented by a change in the sonic speed or the attenuation coefficient and a change in the wave height or the frequency spectrum of the bottom surface wave.

Then, as a result of the investigation, it has been found that when attention is focused on a change in the ultrasonic signal caused by a change in the crystal-grain physical properties, diagnosis of even fine microstructures can be achieved easily with precision.

That is, in a case that ultrasonic is projected into a material and then an ultrasonic wave form, for example, shown in the upper part of FIG. 5 is obtained, frequency conversion is performed on the first bottom surface wave and the second bottom surface wave in the obtained ultrasonic wave form so that the frequency spectrums of the first bottom surface wave and the second bottom surface wave are calculated as shown in the lower part of FIG. 5. Then, with using amplitudes $P_1$ (in an arbitrary unit) and $P_2$ (in an arbitrary unit) at a predetermined frequency, an attenuation coefficient $\alpha$ (neper/m) shown in (Formula 1) is obtained. Here, in (Formula 1), d denotes a material thickness (m).

[Mathematical Expression 1]

$$\alpha = \ln\left(\frac{P_1}{P_2}\right)\bigg/ 2d \quad (1)$$

$\alpha$: Attenuation coefficient
$P_1$: Amplitude of the First bottom surface wave
$P_2$: Amplitude of the Second bottom surface wave
$d$: Thickness The present inventors have focused attention on a fact that when the material is polycrystalline like an object material of the present invention and the crystal grain diameter is far smaller than the wavelength of the projected ultrasonic (Rayleigh scattering region), as for an attenuation coefficient $\alpha_L$ of the longitudinal wave projected into a material (a polycrystalline material), the above-mentioned attenuation coefficient $\alpha$ can be expressed also by a formula employing crystal-grain physical property values as variables as in the following (Formula 2).

[Mathematical Expression 2]

$$\alpha_L = \frac{8\pi^3}{375} \frac{V f^4}{\rho^2} \frac{A^2}{v_L^8}\left[2 + 3\left(\frac{v_L}{v_T}\right)^5\right] \quad (2)$$

$\alpha_L$: Attenuation coefficient of longitudinal wave
$V$: Volume of crystal-grain
$f$: Frequency of ultrasonic
$v_L$: Longitudinal wave sonic speed
$v_T$: Transverse wave sonic speed
$A$: Acoustic anisotropy
$\rho$: Density In (Formula 2), the attenuation coefficient $\alpha_L$ of the longitudinal wave is inversely proportional to the square of the density $\rho$ serving as a crystal-grain physical property value and to the eighth power of the sonic speed $v_L$ of the longitudinal wave. Thus, it is recognized that when the crystal-grain physical property varies, even in a case that a change in the physical property value such as the ultrasonic sonic speed in association with the occurrence of fine microstructures is small, a large change appears in the attenuation coefficient $\alpha_L$ of the longitudinal wave. Further, the attenuation coefficient $\alpha_L$ of the longitudinal wave is proportional to the volume $V$ of the crystal grain. Thus, in correspondence to the large change in the attenuation coefficient $\alpha_L$ of the longitudinal wave, a large change appears in the volume V of the crystal grain. That is, a small change in the physical property value associated with the occurrence of fine microstructures can be recognized as a large change in the volume of the crystal grain.

On the basis of the above-mentioned findings, the present inventors have recognized that the amount of occurrence of microstructures in a material can easily be quantified by using the following technique.

That is, first, ultrasonic is projected into a material of a state without the occurrence of microstructures and then, from the bottom surface wave reflected from material, the attenuation coefficient is calculated for each frequency by using (Formula 1). Then, by using the density and the sonic speed acquired separately according to a method described below and by using the attenuation coefficient calculated above, the volume of the crystal grain prior to the occurrence of microstructures is calculated in advance according to (Formula 2). At that time, the volume of the crystal grain does not relate to the frequency and remains at a fixed value. Then, ultrasonic is projected into the material serving as a diagnosis object and thereby the attenuation coefficient is calculated for each frequency similarly to the above-mentioned case. After that, the volume of the crystal grain after the occurrence of microstructures is calculated.

Then, the difference between the volume of the crystal grain before the occurrence of microstructures and the volume of the crystal grain after the occurrence of microstructures (the amount of volume change) having been calculated is a volume change associated with the occurrence of microstructures. Thus, this value can be regarded as the amount of occurrence of microstructures. Hence, by applying the above-mentioned method, the amount of occurrence of microstructures can be quantified.

Here, as shown in FIG. 4, the longitudinal-wave sonic speed can be acquired using the ultrasonic wave form as the time elapsing from incidence of ultrasonic projected into the material of thickness d to emergence of the first bottom surface wave. Here, the density may be acquired in advance. Alternatively, the density may be calculated from a reference material or a literature value may be employed. Further, the acoustic anisotropy may be calculated in advance from a reference material. Alternatively, a literature value may be employed. Further, the longitudinal-wave sonic speed and the traverse-wave sonic speed can be calculated, for example, from the following publicly known formula employing Poisson's ratio, Young's modulus, and the density.

[Mathematical Expression 3]

$$V_L = \sqrt{\frac{E(1-v)}{\rho(1+v)(1-2v)}}$$
$$V_T = \sqrt{\frac{E}{\rho 2(1+v)}} \implies \frac{V_T}{V_L} = \sqrt{\frac{(1-2v)}{2(1-v)}}$$

$V_L$: Longitudinal wave sonic speed $V_T$: Transverse wave sonic speed $E$: Young's modulus $\rho$: Density $v$: Poisson's ratio Here, in the above description, with employing an identical material, before (an initial state) and after the occurrence of microstructures, ultrasonic was projected and then the attenuation coefficient was calculated for each frequency according to (Formula 1) on the basis of the bottom surface wave reflected from the material. In place of the method that the occurrence of microstructures is quantified by using an identical material, a material of the same kind as the material serving as a diagnosis object and of a state without the occurrence of microstructures may be prepared separately. Then, ultrasonic may be projected into this and similar measurement may be performed. Then, the obtained data may be employed as the data of a material without the occurrence of microstructures.

Further, in place of employing the above-mentioned data of a material without the occurrence of microstructures, ultrasonic may be projected and similar measurement may be performed on a diagnosis material in which microstructures have already occurred in the time course and in which the amount of occurrence of microstructures is known in advance. Then, the obtained data may be employed. In this case, the temporal change in the amount of occurrence of microstructures in the diagnosis material can be recognized.

The inventions according to claims 1, 2, and 3 are inventions based on the above-mentioned findings.

That is, the invention according to claim 1 is a material diagnostic method of performing non-destructive diagnosis of microstructures occurring in a material by using ultrasonic, wherein with utilizing a fact that a change in physical properties of crystal grain caused by microstructures affects ultrasonic scattering, a change in the ultrasonic scattering by crystal grains is recognized from bottom surface wave and back-scattered wave so that an amount of change in the microstructures is quantified.

Further, the invention according to claim 2 is a material diagnostic method of performing non-destructive diagnosis of microstructures occurring in a material by using ultrasonic, comprising:

an initial crystal grain volume calculation step of projecting ultrasonic into a material of a state without occurrence of microstructures so as to obtaining an ultrasonic wave form, then calculating an attenuation coefficient for each frequency from frequency spectrums of first bottom surface wave and second bottom surface wave obtained by performing frequency conversion on the ultrasonic wave form, further acquiring a density of the material and a sonic speed of the ultrasonic, and then calculating a volume of a crystal grain from the obtained attenuation coefficient, the density of the material, and the sonic speed of the ultrasonic;

a diagnosis object crystal grain volume calculation step of projecting ultrasonic into a material serving as a diagnosis object so as to obtain an ultrasonic wave form and then calculating a volume of a crystal grain of the diagnosis object by a method same as the initial crystal grain volume calculation step; and a microstructure occurrence amount quantification step of calculating an amount of volume change of the crystal grain from the individual volumes obtained at the initial crystal grain volume calculation step and the diagnosis object crystal grain volume calculation step and thereby quantifying an amount of occurrence of microstructures.

Further, the invention according to claim 3 is a material diagnostic method of performing non-destructive diagnosis of microstructures occurring in a material by using ultrasonic, comprising:

a first crystal grain volume calculation step of projecting ultrasonic into any one of a material serving as a diagnosis object and being in an initial state, a material of the same kind as the material serving as a diagnosis object and of a state without occurrence of microstructures, and a material serving as a diagnosis object and being in a state that the amount of occurrence of microstructures is known in advance, so as to obtaining an ultrasonic wave form, then calculating an attenuation coefficient for each frequency from frequency spectrums of first bottom surface wave and second bottom surface wave obtained by performing frequency conversion on the ultrasonic wave forms, further acquiring a density of the material and sonic speed of the ultrasonic, and then calculating a volume of a crystal grain from the obtained attenuation coefficient, the density of the material, and the sonic speed of the ultrasonic;

a second crystal grain volume calculation step of projecting ultrasonic into a material serving as a diagnosis object so as to obtain an ultrasonic wave form and then calculating a volume of a crystal grain of the diagnosis object by a method same as the first crystal grain volume calculation step; and a microstructure occurrence amount quantification step of calculating an amount of volume change of the crystal grain from the individual volumes obtained at the first crystal grain volume calculation step and the second crystal grain volume calculation step and thereby quantifying an amount of occurrence of microstructures.

In the inventions of claims 2 and 3, the volume of the crystal grain is obtained directly from the attenuation coefficient and the amount of occurrence of microstructures is quantified from the change in the volume of the crystal grain. Instead, the amount of occurrence of microstructures, that is, the amount of volume change of the crystal grain, may be assumed in advance and then, on the basis of the assumption, the attenuation coefficient and the frequency spectrum may be obtained by according to (Formula 2). Then, when with variously changing the assumption for the amount of occurrence of microstructures, comparison with the frequency spectrum obtained from the diagnosis material is repeated, the amount of occurrence of microstructures can be quantified more easily.

Here, at that time, the amount of change in the sonic speed can be acquired from the ultrasonic signal from the material with the occurrence of microstructures. However, also when a value obtained in accordance with past findings is employed, quantification can be achieved satisfactorily in practice.

(2) Next, quantification of the depth distribution of fine microstructures occurring in a material is described below.

By applying the above-mentioned method, the amount of occurrence of microstructures is quantified. Nevertheless, the microstructures such as precipitates and voids have a depth distribution. Thus, in addition to the amount of occurrence, the depth distribution also need be quantified.

At the time of quantification of the depth distribution of microstructures, the present inventors have focused attention on the backscattered wave of the ultrasonic. That is, the bottom surface wave is a signal affected by the entirety in the inside of the material. Thus, an average physical property value of the material through which the ultrasonic have passed and reflected can be calculated. In contrast, the backscattered wave is a weak signal but yet a signal reflected from a particular depth, and hence has information concerning the depth distribution. Thus, the present inventors have thought that the depth distribution can be calculated.

The backscattered wave of the ultrasonic are defined by the following (Formula 3) and include the attenuation coefficient $\alpha$ as a variable. Then, as described above, a large change appears in the change in the attenuation coefficient even when a change in the crystal-grain physical property values is small. Thus, the backscattered wave also varies largely and hence the depth distribution can be quantified even for fine microstructures.

[Mathematical Expression 4]

$$P(x, \omega) = CP_0(\omega)\sqrt{\left(\frac{d\gamma}{d\Omega}\right)_{L,\pi} \exp(-2\alpha x)} \quad (3)$$

$P(x, \omega)$: Scattered wave sound pressure reflected from depth $x$ $C$: Constant determined by the material $P_0(\omega)$: Projecting sound pressure of frequency $\omega$ component $\left(\frac{d\gamma}{d\Omega}\right)_{L,\pi}$: Differential cross-section of reflection of Longitudinal wave in $\pi$ direction $\alpha$: Attenuation coefficient Specifically, first, the backscattered wave region of the ultrasonic wave form acquired by projecting ultrasonic into the material serving as a diagnosis object is divided into particular depth intervals. Then, frequency conversion is performed on each interval so that the frequency spectrum of the backscattered wave is calculated for each interval.

Then, with assuming a depth distribution of the microstructures in the material, the frequency spectrum of the backscattered wave is calculated for each identical interval according to (Formula 3).

At that time, the frequency spectrum of the backscattered wave is calculated by using a differential cross section $(d\gamma/d\Omega)_{L,n}$ of a cross section $\gamma$ by a solid angle $\Omega$ at each interval of the assumed depth distribution. Here, L denotes the longitudinal wave and n denotes the reflection direction. Then, the differential cross section by crystal grains is calculated by (Formula 4). This (Formula 4) also includes the crystal-grain physical property values as variables. Thus, a change in the crystal-grain physical property values causes a yet larger change in the backscattered wave calculated by (Formula 3).

[Mathematical Expression 5]

$$\left(\frac{d\gamma}{d\Omega}\right) = \frac{1}{4\pi}\frac{8\pi^3}{375}\frac{Vf^4}{\rho^2}\frac{A^2}{v_L^8}\left[2 + 3\left(\frac{v_L}{v_t}\right)^5\right] \quad (4)$$

$\left(\frac{d\gamma}{d\Omega}\right)$: Differential cross-section $V$: Volume of crystal-grain $f$: Frequency of ultrasonic $v_L$: Longitudinal wave sonic speed $v_T$: Transverse wave sonic speed $A$: Acoustic anisotropy $\rho$: Density Then, the frequency spectrum of the backscattered wave calculated on the basis of the assumed depth distribution of the microstructures in the material and the frequency spectrum of the backscattered wave obtained above are compared with each other. Then, comparison is repeated with variously changing the assumption, until both accurately agree with each other.

As such, when the frequency spectrum of the backscattered wave calculated on the basis of the assumption is compared with the frequency spectrum of the backscattered wave obtained from the diagnosis object, the depth distribution of the microstructures can easily be quantified.

Further, the above-mentioned quantification of the depth distribution of the microstructures can be achieved also when the integrated intensity area ratio of the frequency spectrum of the backscattered wave calculated on the basis of the assumed depth distribution of the microstructures in the material and the integrated intensity area ratio of the frequency spectrum of the individual backscattered wave calculated from the obtained frequency spectrum of the backscattered wave are compared with each other and then comparison is repeated with variously changing the assumption, until both accurately agree with each other.

The inventions according to claims 4 and 5 are inventions based on the above-mentioned findings.

That is, the invention according to claim 4 is a material diagnostic method of performing non-destructive diagnosis of microstructures occurring in a material by using ultrasonic, comprising:

a diagnosis object frequency spectrum calculation step of dividing a backscattered wave region of an ultrasonic wave form acquired by projecting ultrasonic into a material serving as a diagnosis object and having an already-known amount of occurrence of microstructures, into intervals of predetermined width in a depth direction of the material, and then calculating a frequency spectrum of the backscattered wave by using frequency conversion for each interval; and a microstructure depth distribution quantification step of, with assuming a depth distribution of the microstructures and comparing the frequency spectrum of the backscattered wave calculated for each interval identical to that at the diagnosis object frequency spectrum calculation step, determining the depth distribution of the microstructures so as to quantify the depth distribution of the microstructures in the material serving as a diagnosis object.

Further, the invention according to claim 5 is a material diagnostic method of performing non-destructive diagnosis of microstructures occurring in a material by using ultrasonic, comprising:

a diagnosis object frequency spectrum integrated-intensity area ratio calculation step of dividing a backscattered wave region of an ultrasonic wave form acquired by projecting ultrasonic into a material serving as a diagnosis object and having an already-known amount of occurrence of microstructures, into intervals of predetermined width in a depth direction of the material, and then calculating an integrated intensity area ratio of the frequency spectrum of the backscattered wave for each interval by using frequency conversion; and a microstructure depth distribution quantification step of, with assuming a depth distribution of the microstructures and comparing the integrated intensity area ratio of the frequency spectrum of the backscattered wave calculated for each interval identical to that at the diagnosis object frequency spectrum integrated-intensity area ratio calculation step, determining the depth distribution of the microstructures so as to quantify the depth distribution of the microstructures in the material serving as a diagnosis object.

(3) Next, quantification of the depth distribution of fine microstructures composed of dislocations occurring in a material is described below.

In addition to voids and precipitates described above, the kinds of microstructures include microstructures composed of dislocations. In the case of microstructures composed of dislocations, the depth distribution of dislocation density need be obtained.

Here, the present inventors have recognized that in contrast to precipitates and voids, in dislocations, scattering of ultrasonic does not occur and absorption alone occurs and that the absorption of the ultrasonic causes a decrease in the backscattered wave. Then, the present inventors have focused attention on a fact that the ultrasonic absorption caused by dislocations, that is, the attenuation $\alpha(\omega)$, can be expressed by the following (Formula 5).

[Mathematical Expression 6]

$$\alpha(\omega) = 8.68 \times 10^{-6} \frac{4\mu b^2}{\pi^4 C} \Lambda L^2 \omega_0 \frac{(d/\omega_0)(\omega/\omega_0)^2}{[1-(\omega/\omega_0)^2]^2 + (\omega/\omega_0)^2(d/\omega_0)^2} \quad (5)$$

$\alpha(\omega)$: Attenuation $\Lambda$: Dislocation density $L$: Average dislocation length $\omega_0$: Characteristic frequency of dislocation Here, in (Formula 5), $\mu$ is a modulus of rigidity, b is a Berger spectrum, and C is a tension of dislocation. These are respectively obtained from the lattice constant, the density, the modulus of rigidity, and the Poisson's ratio according to the following formulas.

[Mathematical Expression 7]

$$C = \frac{2\mu b^2}{\pi(1-\nu)}$$

$$d = \frac{B}{\pi \rho b^2}$$

$\mu$: Modulus of rigidity $B$: $5 \times 10^{-5} \sim 5 \times 10^{-3}$ $\nu$: Poisson's ratio $\rho$: Density Further, an average dislocation length L is difficult to be measured and hence is acquired in advance from the lattice constant or from a reference. Then, a characteristic frequency $\omega_0$ of the dislocation is determined by the average dislocation length L as shown in the following formula. It is known that the value is of GHz order.

[Mathematical Expression 8]

$$\omega_0 = \sqrt{\frac{\pi C}{L^2 \rho b^2}}$$

Then, the present inventors have recognized that the depth distribution of dislocation density in a material can easily be quantified by using the following technique.

That is, first, ultrasonic is projected into a material whose dislocation density and crystal grain diameter are known in advance, and thereby the frequency spectrum of the backscattered wave caused by crystal grains is calculated for each depth.

Then, a depth distribution of dislocation density in the material is assumed. The backscattered wave caused by the crystal grains are absorbed and attenuated by dislocations present in the path of the ultrasonic. The magnitude of attenuation can be obtained by using (Formula 5). From the above-mentioned method, the backscattered-wave frequency spectrum is calculated for each depth.

That is, the amount of decrease of backscattered-wave frequency spectrum obtained from the two backscattered-wave frequency spectrums can be regarded as the amount of absorption of the ultrasonic caused by the dislocations. Thus, the frequency spectrum of the backscattered wave calculated on the basis of this assumption and the frequency spectrum of the backscattered wave obtained above are compared with each other. Then, until both accurately agree with each other, comparison is repeated with variously changing the assumption, so that the dislocation depth distribution in the material can be quantified.

Also by the following method, the dislocation depth distribution in the material can be quantified. Similarly to the above-mentioned case, the integrated intensity area ratio of the frequency spectrum of the backscattered wave calculated on the basis of the assumption and the integrated intensity area ratio of the frequency spectrum of the individual backscattered wave calculated from the obtained frequency spectrum of the backscattered wave are compared with each other and then comparison is repeated with variously changing the assumption, until both accurately agree with each other.

The inventions according to claims 6 and 7 are inventions based on the above-mentioned findings.

That is, the invention according to claim 6 is a material diagnostic method of performing non-destructive diagnosis of microstructures occurring in a material by using ultrasonic, comprising:

a diagnosis object frequency spectrum calculation step of dividing a backscattered wave region of an ultrasonic wave form acquired by projecting ultrasonic into a material serving as a diagnosis object and having already-known dislocation density and crystal grain diameter, into intervals of predetermined width in a depth direction of the material, and then calculating a frequency spectrum of the backscattered wave by using frequency conversion for each interval;

a comparison-use frequency spectrum calculation step of, with assuming a depth distribution of the microstructures, calculating the frequency spectrum for each interval identical to that at the diagnosis object frequency spectrum calculation step; and a microstructure dislocation depth distribution quantification step of determining the depth distribution of the microstructures in the material from the amount of decrease between the frequency spectrums obtained at the diagnosis object frequency spectrum calculation step and at the comparison-use frequency spectrum calculation step and then, on the basis of the determined assumption of the depth distribution of the microstructures, quantifying the dislocation depth distribution of the microstructures in the material serving as a diagnosis object.

Further, the invention according to claim 7 is a material diagnostic method of performing non-destructive diagnosis of microstructures occurring in a material by using ultrasonic, comprising:

a diagnosis object frequency spectrum integrated-intensity area ratio calculation step of dividing a backscattered wave region of an ultrasonic wave form acquired by projecting ultrasonic into a material serving as a diagnosis object and having already-known dislocation density and crystal grain diameter, into intervals of predetermined width in a depth direction of the material, and then calculating an integrated intensity area ratio of the frequency spectrum of the backscattered wave for each interval by using frequency conversion;

a comparison-use frequency spectrum integrated-intensity area ratio calculation step of, with assuming a depth distribution of the microstructures, calculating the integrated intensity area ratio of the frequency spectrum for each interval identical to that at the diagnosis object frequency spectrum integrated-intensity area ratio calculation step; and a microstructure dislocation depth distribution quantification step of determining the depth distribution of the microstructures in the material from the integrated intensity area ratio of the frequency spectrum obtained at the diagnosis object frequency spectrum integrated-intensity area ratio calculation step and at the comparison-use frequency spectrum integrated-intensity area ratio calculation step and then, on the basis of the determined assumption of the depth distribution of the microstructures, quantifying the dislocation depth distribution of the microstructures in the material serving as a diagnosis object.

(4) Next, description is given for a case that plural kinds of fine microstructures occur in a material.

The above-mentioned microstructures such as precipitates, voids, and dislocations are not necessarily occur separately and a plurality of kinds of microstructure occurs simultaneously in some cases.

Thus, the present inventors have investigated a method that the kinds are distinguished for microstructures having occurred and then estimation and quantification are performed on each kind of microstructures.

As a result, it has been recognized that with adopting as indicators the sonic speed and the attenuation coefficient of the ultrasonic, the bottom surface wave frequency spectrum, and the backscattered-wave frequency spectrum described above, analysis is performed on each indicator obtained by projecting ultrasonic into a material serving as a diagnosis object with taking into consideration: each indicator acquired in advance by projecting ultrasonic into any one of a material serving as a diagnosis object and being in an initial state (a state without the occurrence of microstructures), a material of the same kind as the material serving as a diagnosis object and of a state without the occurrence of microstructures, and a material serving as a diagnosis object and being in a state that the amount of occurrence of microstructures is known in advance; the usage history of the material; and the like, then, these indicators appear characteristically depending on the kinds of microstructures and hence microstructures such as precipitates, voids, and dislocations can be distinguished easily. Further, it has been recognized that such distinction of these microstructures can be achieved even when one indicator is employed, for example, even when the sonic speed is employed as an indicator in a case of two microstructures consisting of dislocations and precipitates (carbide).

Here, the above-mentioned expression "taking into consideration the usage history of the material and the like" means that operating environments such as the operating temperature, the dose of irradiation, and the operating time are taken into consideration.

The invention according to claim 8 is an invention based on the above-mentioned findings, and is a material diagnostic method of performing non-destructive diagnosis of microstructures occurring in a material by using ultrasonic, wherein kinds of microstructures having occurred are distinguished by using one or more indicators selected from: a sonic speed and an attenuation coefficient of ultrasonic; a frequency spectrum, a low-frequency-side wave height, and a high-frequency-side wave height of bottom surface wave; a frequency spectrum of backscattered wave; and an integrated intensity area ratio of a frequency of backscattered wave, which are obtained by projecting ultrasonic into a material, and on the basis of: a change between standard material data acquired in advance from any one of a material serving as a diagnosis object and being in an initial state, a material of the same kind as the material serving as a diagnosis object and of a state without the occurrence of microstructures, and a material serving as a diagnosis object and being in a state that the amount of occurrence of microstructures is known in advance and diagnosis object material data obtained at the time of diagnosis; and a usage history of the material.

When the diagnostic methods of claims 1 to 7 are applied, the amount of occurrence or the depth distribution can be estimated or quantified for each microstructure defect distinguished by the invention of the present claim.

(5) As described above, the present inventors have found that in place of performing diagnosis of microstructures with focusing attention only on a change in the backscattered wave intensity of the ultrasonic signal waveform like in the conventional art, when analysis is performed with taking into consideration a change in the crystal-grain physical property values (such as the volume, the density, and the sonic speed) associated with the occurrence of microstructures such as precipitates of carbide or the like, voids, dislocations, and phase transformation, diagnosis can be achieved easily with precision even for fine microstructures.

That is, the invention according to claim 9 is a material diagnostic method of performing non-destructive diagnosis of microstructures occurring in a material by using ultrasonic, comprising:

a first data acquisition step of projecting ultrasonic into any one of a material serving as a diagnosis object and being in an initial state, a material of the same kind as the material serving as a diagnosis object and of a state without the occurrence of microstructures, and a material serving as a diagnosis object and being in a state that the amount of occurrence of microstructures is known in advance, and thereby acquiring an ultrasonic wave form and a crystal-grain physical property value of the material; and a second data acquisition step of projecting ultrasonic into the material serving as a diagnosis object and thereby acquiring an ultrasonic wave form and a crystal-grain physical property value of the material, wherein with taking into consideration a change in the crystal-grain physical property value obtained at the first data acquisition step and at the second data acquisition step, the ultrasonic wave form is evaluated so that diagnosis of microstructures occurring in the material is performed.

Further, the invention according to claim 10 is the material diagnostic method according to claim 9, wherein the microstructures occurring in the material are microstructures consisting of any one or more of precipitates, void, dislocation, and phase transformation.

Effect of the Invention

According to the present invention, a material diagnostic method can be provided in which even for fine microstructures of approximately several tens of μm or smaller, estimation and quantification of a material are performed in a non-destructive manner with satisfactory precision concerning the kind, the amount of occurrence, the depth distribution, and the like thereof so that diagnosis can be achieved.

MODE OF IMPLEMENTING THE INVENTION

1. Quantitative Evaluation of Microstructure Occurrence Amount in Case of Uniform Distribution The following description relates to a method of quantitative evaluation of the microstructure occurrence amount in a case that microstructures are distributed uniformly in a material of a hexagonal bar of stainless steel having a thickness of 52.23 mm.

(1) Acquisition of Ultrasonic Data of Material of State without Occurrence of Microstructures First, an ultrasonic signal having a peak frequency of 10 MHz was projected, by an ultrasonic transducer, into a material (a non-irradiated archive material) of a state without the occurrence of microstructures so that an ultrasonic wave form was acquired by the ultrasonic transducer by converting reflections of the ultrasonic signal.

(2) Acquisition of Ultrasonic Data of Material with Occurrence of Microstructures With focusing attention on a change in the physical property value of the crystal grain (a change in the sonic speed was employed here) caused by the occurrence of assumed microstructures, the frequency spectrum was calculated on the basis of the amount of change in the attenuation coefficient. Detailed examples of calculation are described below for individual cases of microstructures caused by voids, precipitates, and dislocations.

(a) Case of Microstructures Caused by Voids

As microstructures, microstructures caused by void swelling having a swelling of 1.3% were assumed. Then, the attenuation coefficient $\alpha_L$ was calculated for each frequency by using (Formula 2) so that the frequency spectrum of the bottom surface wave was calculated. In accordance with past findings, the amount of change in the sonic speed caused by the occurrence of void swelling having a swelling of 1.3% was assumed to be 0.7%.

Figure 1:
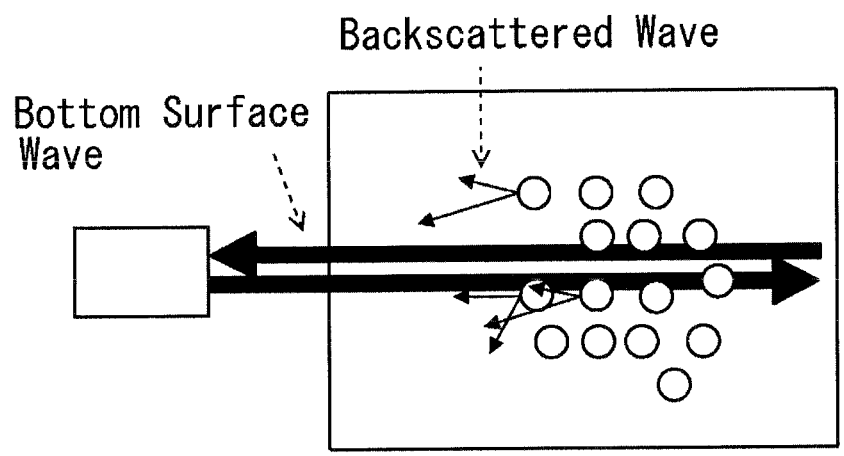
FIG. 1 is a diagram schematically showing a material diagnostic measurement method employing ultrasonic.
Figure 2:
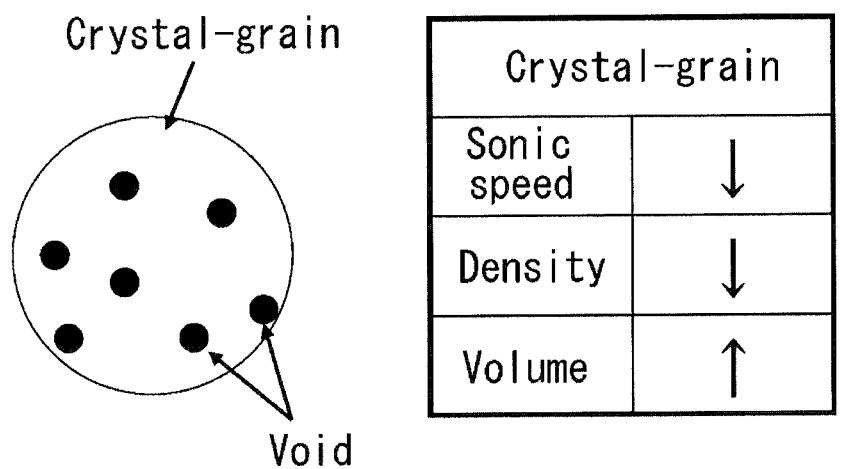
FIG. 2 is a diagram describing a change in physical property values of a crystal grain in a case that voids occur.
Figure 3:
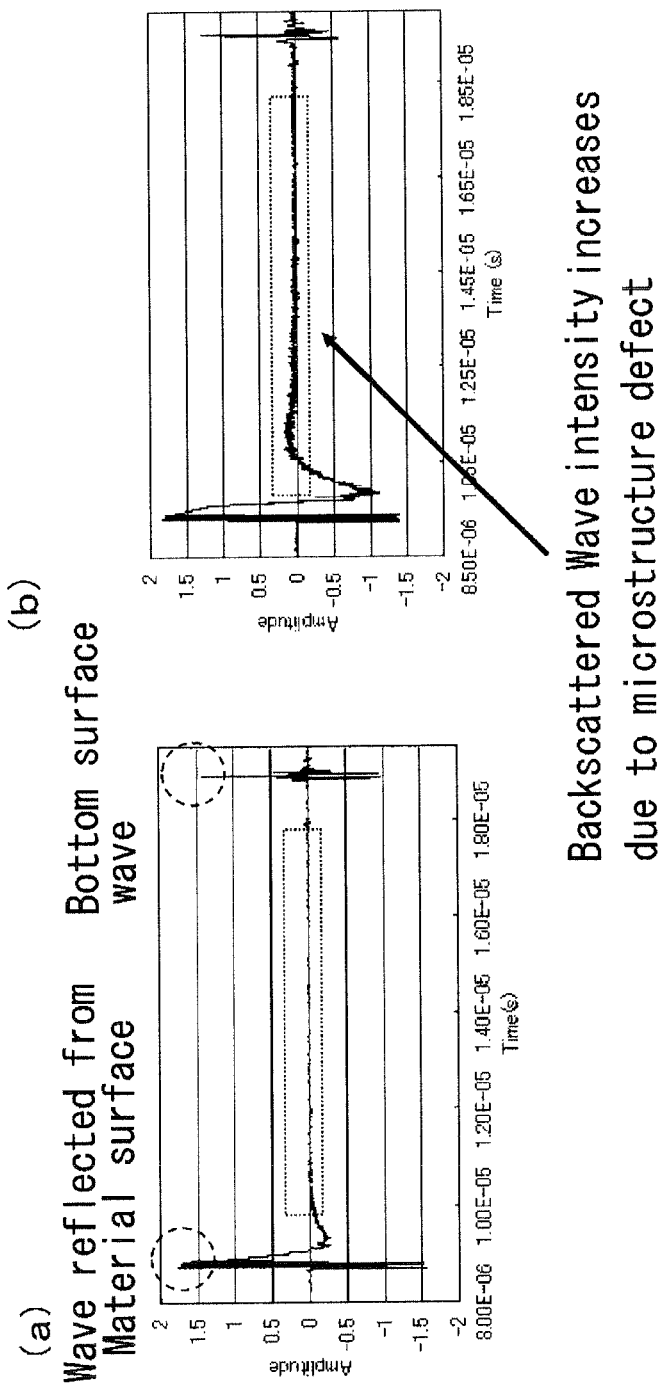
FIG. 3 is a diagram showing an example of a waveform of ultrasonic signal wave observed when ultrasonic is projected into a material.
Figure 4:
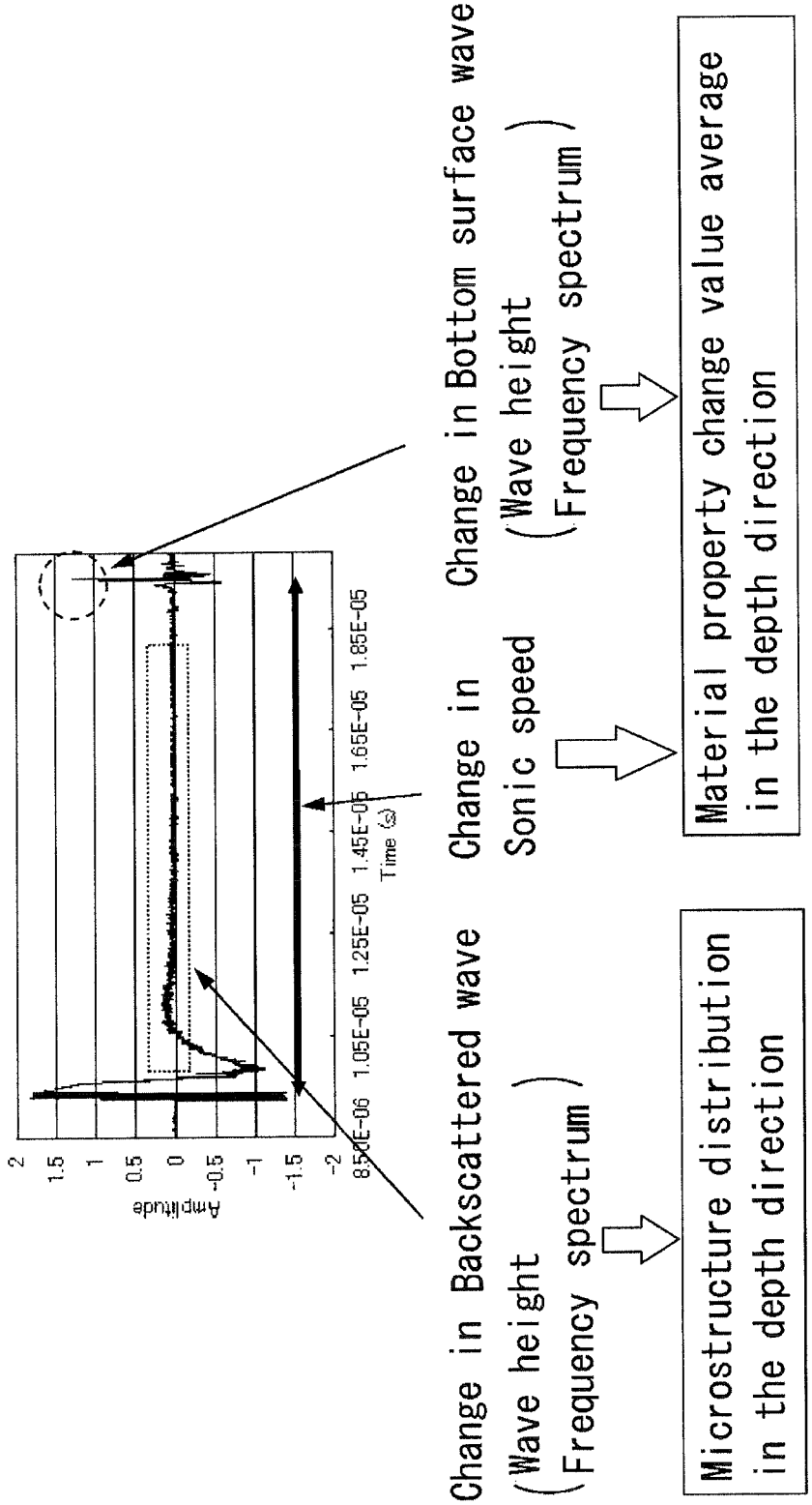
FIG. 4 is a diagram describing relevance between a waveform of ultrasonic signal wave and a microstructure distribution or a material property.
Figure 5:
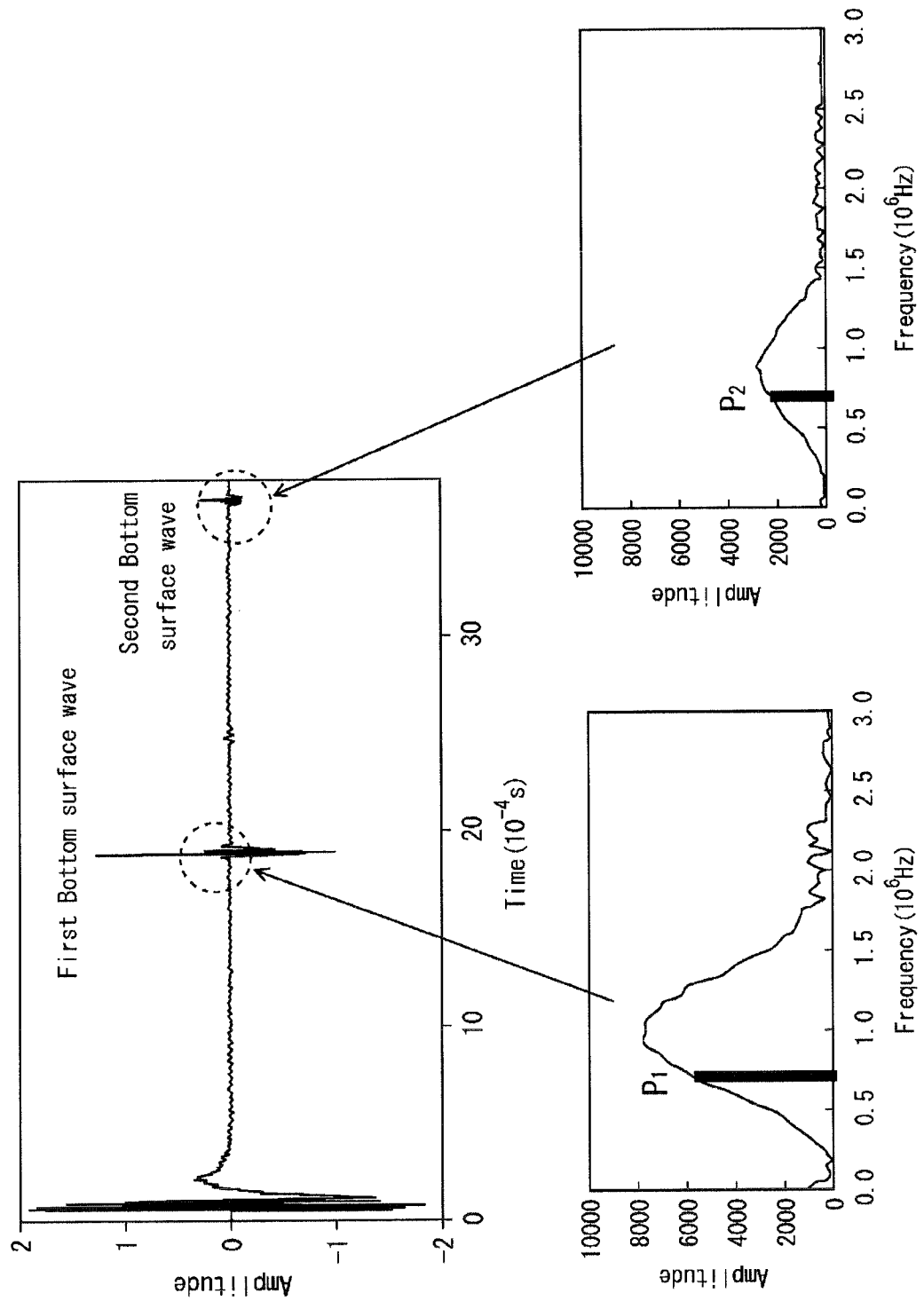
FIG. 5 is a diagram describing a method of calculating an attenuation coefficient on the basis of a frequency spectrum of bottom surface wave.
Figure 6:
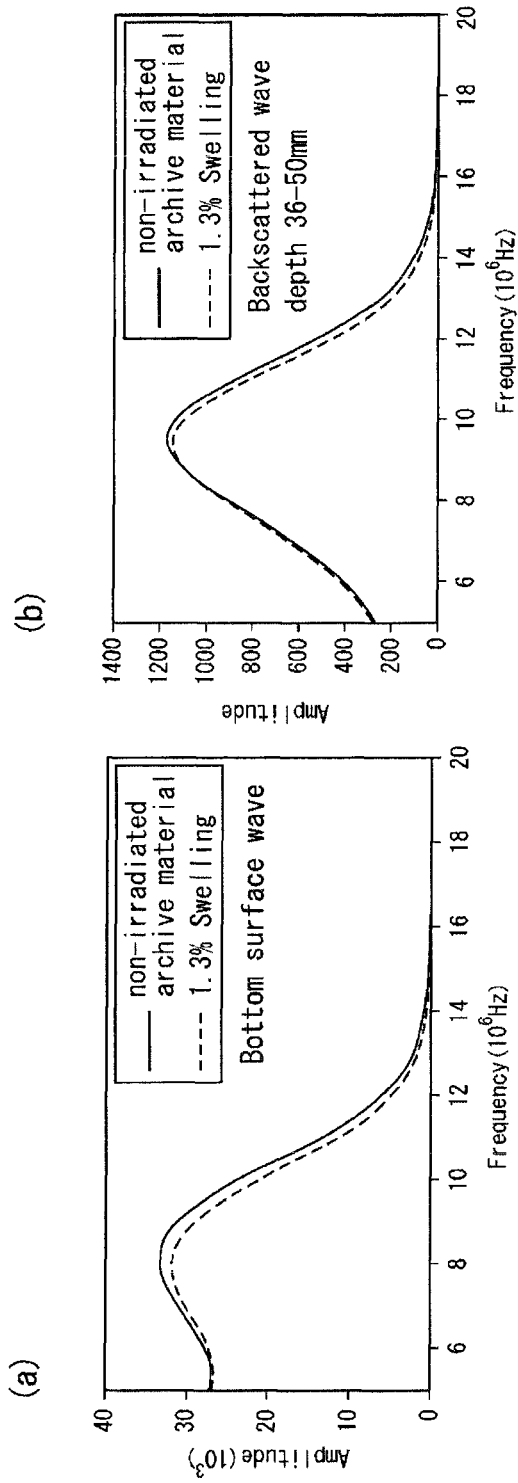
FIG. 6 is a diagram showing frequency spectrums of bottom surface wave and backscattered wave in a case of void swelling of 1.3%.

The calculation results are shown in FIG. 6. Here, from the perspective of the material physical property average and the microstructure depth distribution, FIG. 6 shows (a) the frequency spectrum of the bottom surface wave and (b) the frequency spectrum of the backscattered wave at a depth of 36 to 50 mm. Then, in FIG. 6, a solid line indicates a non-irradiated archive material in which microstructures have not yet occurred and a dashed line indicates a material having a swelling of 1.3%.

As seen from FIG. 6, the data (a solid line) of a case without microstructures and the data (a dashed line) of a case with microstructures can clearly be distinguished from each other.

(b) Case of Microstructures Caused by Precipitates

As microstructures, microstructures having occurred in association with a density increase of 0.6% caused by carbide precipitation were assumed. Then, by using the same method as the above-mentioned one, the frequency spectrum of the bottom surface wave and the frequency spectrum of the backscattered wave were calculated. Here, in accordance with past findings, the amount of change in the sonic speed caused by the density increase of 0.6% caused by carbide precipitation was assumed to be 2%.

Figure 7:
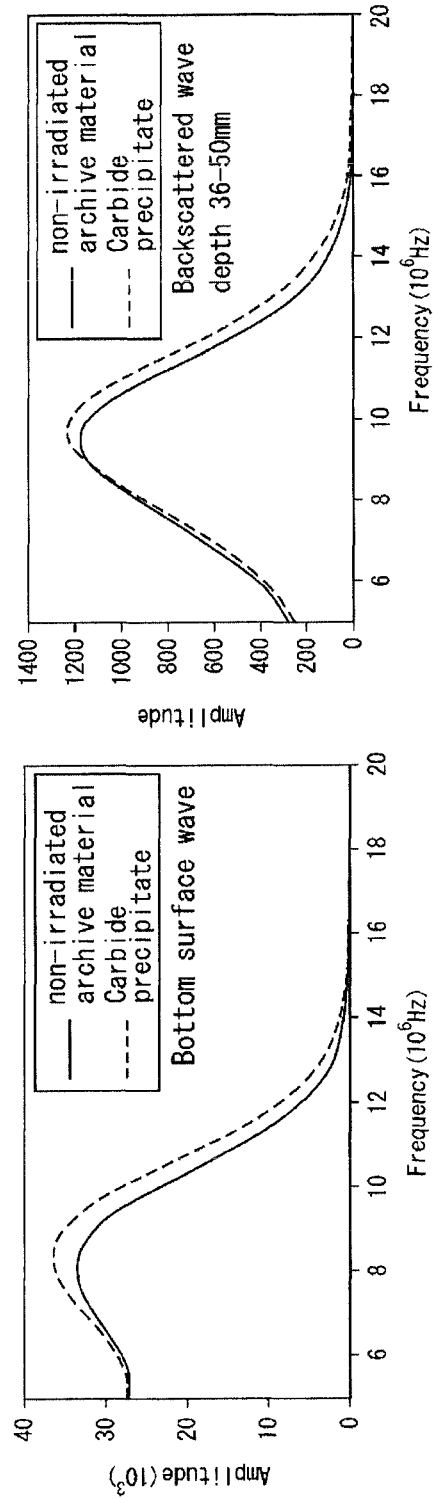
FIG. 7 is a diagram showing frequency spectrums of bottom surface wave and backscattered wave in a case that density has increased by 0.6% by carbide precipitation.

The calculation results are shown in FIG. 7. Here, from a perspective similar to the above-mentioned one, FIG. 7 shows (a) the frequency spectrum of the bottom surface wave and (b) the frequency spectrum of the backscattered wave at a depth of 36 to 50 mm. Then, in FIG. 7, a solid line indicates a non-irradiated archive material in which microstructures have not yet occurred and a dashed line indicates a material in which carbide has been precipitated.

As seen from FIG. 7, the data (a solid line) of a case without microstructures and the data (a dashed line) of a case with microstructures can clearly be distinguished from each other.

(c) Case of Microstructures Caused by Dislocations

As microstructures, microstructures caused by an increase ($10^{15}$ m/m$^3$) in the dislocation density were assumed. Then, by using (Formula 3) and (Formula 5), the attenuation coefficient for each $\omega$ was obtained. Then, with focusing attention on a fact that the attenuation coefficient has been changed in association with a change in the physical property value of the crystal grain, the frequency spectrums of the bottom surface wave and the backscattered wave were calculated with adopting an average dislocation length as a parameter.

Figure 8:
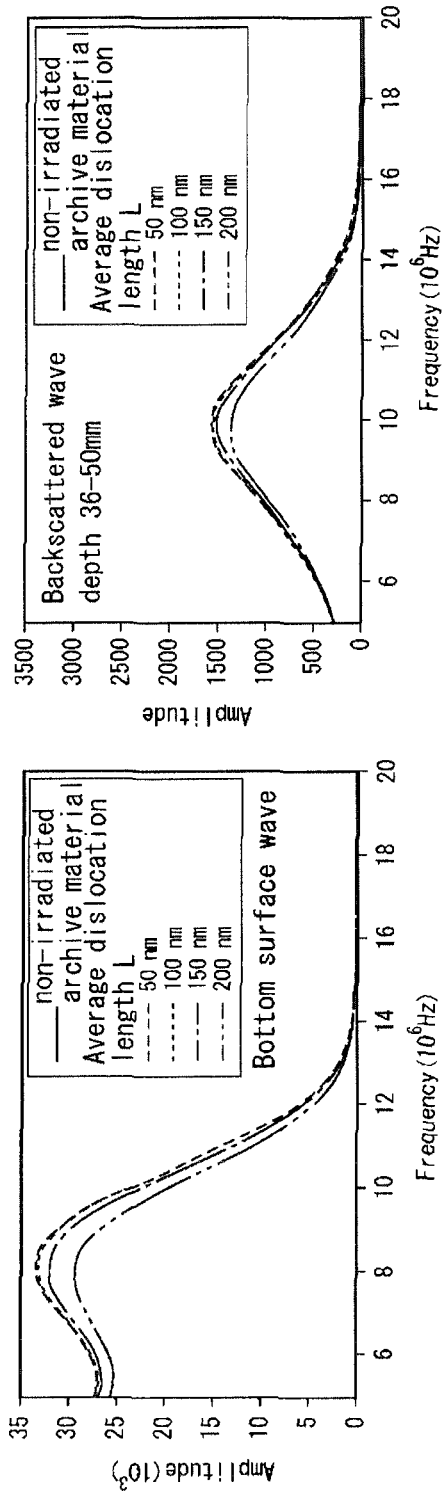
FIG. 8 is a diagram showing frequency spectrums of bottom surface wave and backscattered wave in a case that a dislocation density has increased.

The calculation results are shown in FIG. 8. Here, from a perspective similar to the above-mentioned one, FIG. 8 shows (a) the frequency spectrum of the bottom surface wave and (b) the frequency spectrum of the backscattered wave at a depth of 25 to 39 mm. Then, in FIG. 8, a solid line indicates the frequency spectrum obtained from a non-irradiated archive material in which microstructures have not yet occurred and the other lines indicate frequency spectrums obtained with assumptions that the average dislocation length caused by the dislocation density increase is 50 nm (a dashed line), 100 nm (a dotted line), 150 nm (a dash-dotted line) or 200 nm (a double-dotted chain line).

As seen from FIG. 8, the data (the solid line) of a case without the occurrence of microstructures and the data (the other lines) of cases that microstructures have developed can clearly be distinguished from each other. Further, the difference between average dislocation lengths can also be distinguished clearly from each other.

(3) Discussion

As seen from the results of the individual cases, when with focusing attention on a change in the physical property value of the crystal grain caused by the occurrence of microstructures, the physical property value of the crystal grain is reflected by using each of the above-mentioned formulas, even fine microstructures can clearly be distinguished.

Then, when the present method is applied so that various frequency spectrums are prepared in advance with variously changing each assumption in each case, quantitative evaluation of microstructures can easily be achieved by comparison with the frequency spectrum obtained by projecting ultrasonic onto the material serving as a diagnosis object.

Here, in the description given above, quantitative evaluation of microstructures was performed by using the identical material and by using the time-dependent data of the material of a state (an initial state) without the occurrence of microstructures.

However, in place of performing quantitative evaluation of microstructures by using the identical material, quantitative evaluation of microstructures may be performed by adopting as the data of a non-irradiated archive material the data obtained by measuring a non-irradiated archive material of the same kind.

2. Quantitative Evaluation of Depth Distribution of Microstructures

The following description relates to a method of performing quantitative evaluation of the depth distribution of voids having a depth distribution. Description is given for (A) quantitative evaluation using the backscattered-wave frequency spectrum and, then, for (B) quantitative evaluation using the integrated intensity area ratio of the backscattered-wave frequency spectrum.

(A) Quantitative Evaluation Using Backscattered-Wave Frequency Spectrum (1) Acquisition of Ultrasonic Data of Material of State without Occurrence of Microstructures First, an ultrasonic signal having a peak frequency of 10 MHz was projected, by an ultrasonic transducer, into a material (a non-irradiated archive material) which is composed of a hexagonal bar material of stainless steel having a thickness of 52.23 mm and which is in a state without the occurrence of microstructures, so that an ultrasonic wave form was acquired by the ultrasonic transducer by converting reflections of the ultrasonic signal. Then, with adopting an interval width of 14 mm for the backscattered wave calculation region, the frequency spectrum of the backscattered wave was calculated at depths of 16 to 30 mm and 36 to 50 mm.

(2) Object Material

As materials serving as a diagnosis object, two kinds of materials in which the following microstructures have occurred were assumed.

Figure 9:
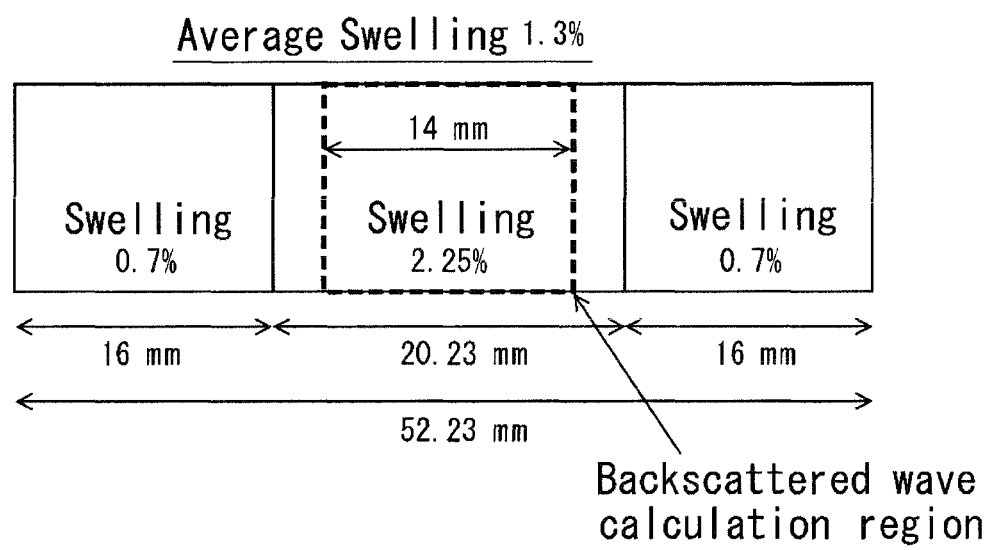
FIG. 9 is a diagram showing a depth distribution of void swelling.

(i) A material in which voids having a swelling of 1.3% are distributed uniformly (ii) A material in which voids having a swelling of 0.7% occur in 16-mm widths at both ends and voids having a swelling of 2.25% occur in a 20.23-mm width in the center part (a 52.23-mm width in total; an average swelling of 1.3%) (see FIG. 9).

(3) Acquisition of Frequency Spectrum of Backscattered Wave

For each diagnosis object material, by using Formula (4) and with adopting an interval width of 14 mm for the backscattered wave calculation region, the frequency spectrums of the backscattered wave were calculated at depths of 16 to 30 mm and 36 to 50 mm.

Figure 10:
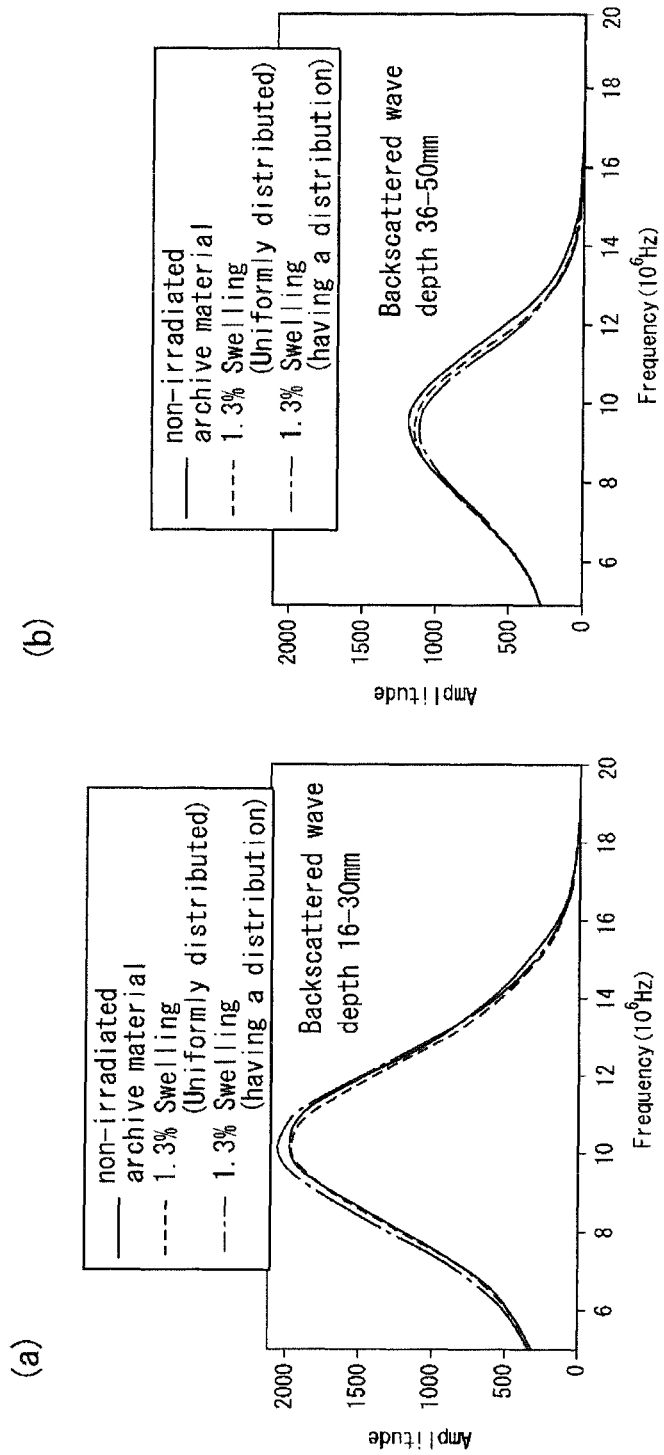
FIG. 10 is a diagram showing a frequency spectrum of backscattered wave at each depth in a case that void swelling has a depth distribution.

The calculation results are shown in FIG. 10. FIG. 10 shows (a) the frequency spectrum of the backscattered wave at a depth of 16 to 30 mm and (b) the frequency spectrum of the backscattered wave at a depth of 35 to 50 mm. Then, a solid line indicates the frequency spectrum obtained from a non-irradiated archive material, a dashed line indicates one obtained from uniform voids, and a dash-dotted line indicates one obtained from voids having a distribution.

As seen from FIG. 10, in either case of (a) and (b), the material without the occurrence of microstructures (the solid line), the material in which uniform voids have occurred (the dashed line), and the material in which voids having a distribution have occurred (the dash-dotted line) can clearly be distinguished from each other.

As such, when with focusing attention on a change in the physical property value of the crystal grain caused by the occurrence of microstructures, and the above-mentioned formula is applied, microstructures having a depth distribution can clearly be distinguished.

Then, when the present method is applied so that with variously changing the assumption of microstructures such as voids, the frequency spectrum of the backscattered wave for each interval is prepared in advance, quantitative evaluation of the depth distribution of microstructures such as voids can easily be achieved by comparison with the frequency spectrum for each interval obtained by projecting ultrasonic onto the material serving as a diagnosis object.

Here, the present inventors have confirmed that also in quantitative evaluation of the depth distribution for dislocations having a depth distribution, the quantitative evaluation can be achieved by operation similar to the above-mentioned one.

(B) Quantitative Evaluation Using Integrated Intensity Area Ratio of Backscattered-Wave Frequency Spectrum (1) Material in which Voids have Occurred and Distributed Uniformly First, with assuming as the material serving as a diagnosis object a material in which voids have occurred and distributed uniformly, the integrated intensity area ratio of the backscattered-wave frequency spectrum was acquired.

Specifically, a material in which voids have occurred and distributed uniformly with a swelling of 0%, 1%, 2%, 3%, or 5% is assumed as a non-irradiated archive material. Then, the integrated intensity of the backscattered-wave frequency spectrum was acquired with changing the depth from the material surface with a depth width of 12 mm for each material. For example, in the calculation at a depth of 42 mm with a swelling of 0%, integration was performed over frequencies of 6 to 9 MHz for the non-irradiated archive material.

Figure 11:
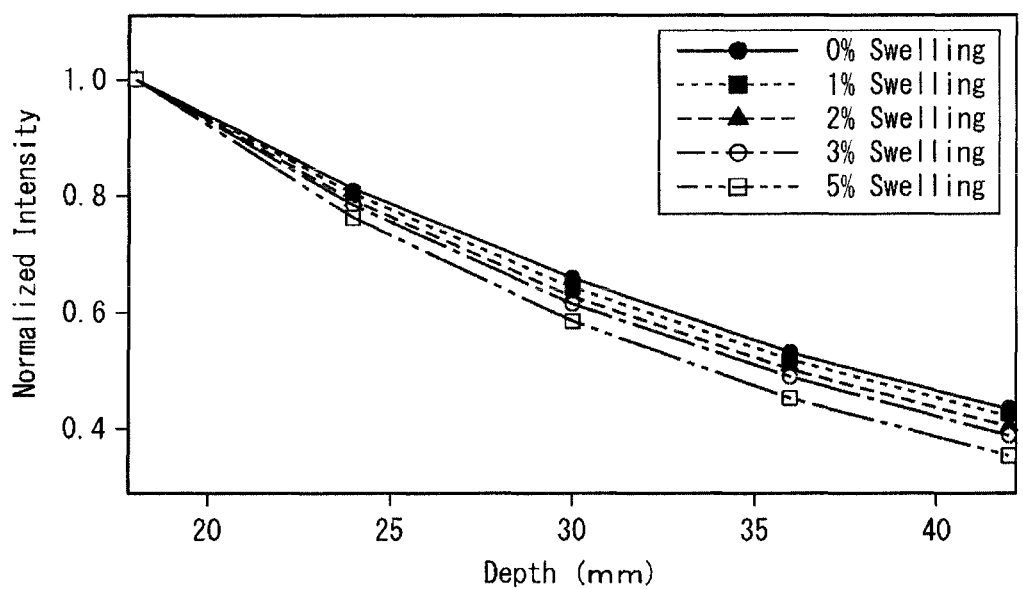
FIG. 11 is a diagram showing an integrated intensity area ratio of a frequency spectrum of backscattered wave at each depth in a case that void swelling is distributed uniformly.

The calculation results are shown in FIG. 11. In FIG. 11, the horizontal axis indicates the depth (mm) from the material surface. Further, the vertical axis indicates the integrated intensity area ratio of the backscattered-wave frequency spectrum obtained by normalizing at a depth of 18 mm the integrated intensity of the backscattered-wave frequency spectrum with a depth width of 12 mm.

As seen from FIG. 11, when voids are distributed uniformly, the integrated intensity area ratio of the backscattered-wave frequency spectrum varies owing to swelling.

(2) Material in which Voids have Occurred with Distribution

Figure 12:
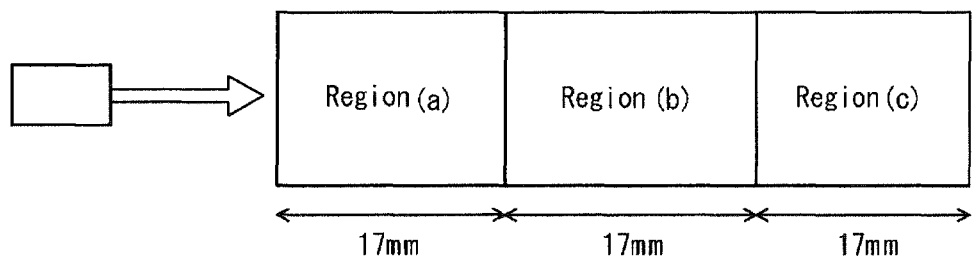
FIG. 12 is a diagram showing a dividing method of dividing a to-be-tested material in a depth direction according to an embodiment of the present invention.

Next, the four kinds of materials in which voids have occurred with the distribution of swelling shown in Table 1 in the regions (a) to (c) shown in FIG. 12 were assumed as materials serving as a diagnosis object. Then, the integrated intensity area ratio of the backscattered-wave frequency spectrum was acquired for each material similarly to the above-mentioned case. Here, as shown in Table 1, in each of these materials, the average swelling is 1% and the average amount of voids is identical.

TABLE 1

| material | region (a) | region (b) | Region (c) | average |
|----------|-----------|-----------|-----------|---------|
| 1 | 1% | 1% | 1% | 1% |
| 2 | 3% | 0% | 0% | 1% |
| 3 | 0% | 3% | 0% | 1% |
| 4 | 0% | 0% | 3% | 1% |

Figure 13:
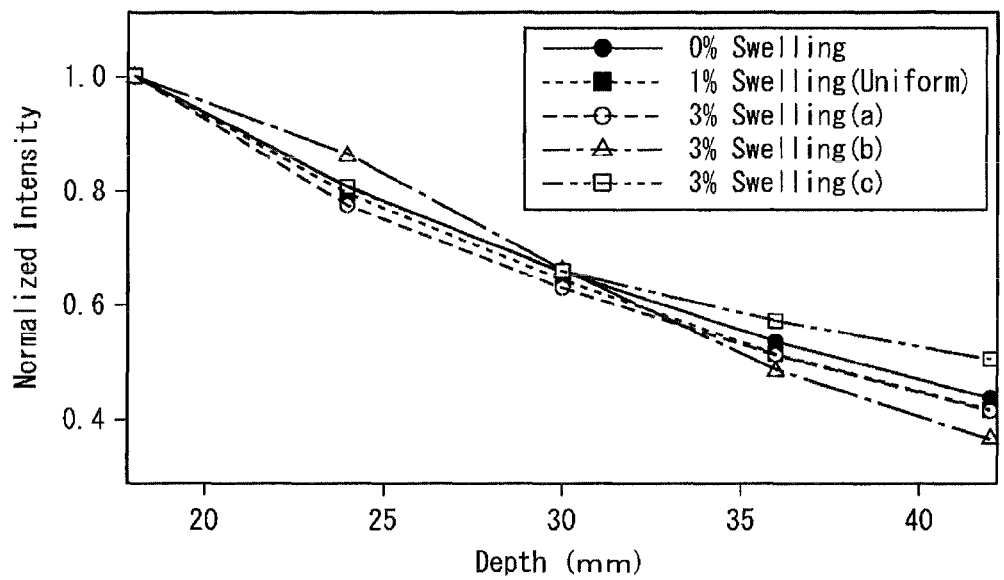
FIG. 13 is a diagram showing an integrated intensity area ratio of a frequency spectrum of backscattered wave at each depth in a case that void swelling has a depth distribution.

The calculation results are shown in FIG. 13. As seen from FIG. 13, despite that the average amount of voids in the entire material is identical to each other, the integrated intensity area ratio of the backscattered-wave frequency spectrum becomes different owing to the distribution of voids.

(3) Comparison Between Experimental Values Obtained from Irradiated Material and Non-Irradiated Material Next, the integrated intensity area ratios of the backscattered-wave frequency spectrum in a non-irradiated archive material of a state without the occurrence of microstructures and in an irradiated material with the occurrence of microstructures were acquired and then compared with each other. The result is shown in FIG. 14.

Figure 14:
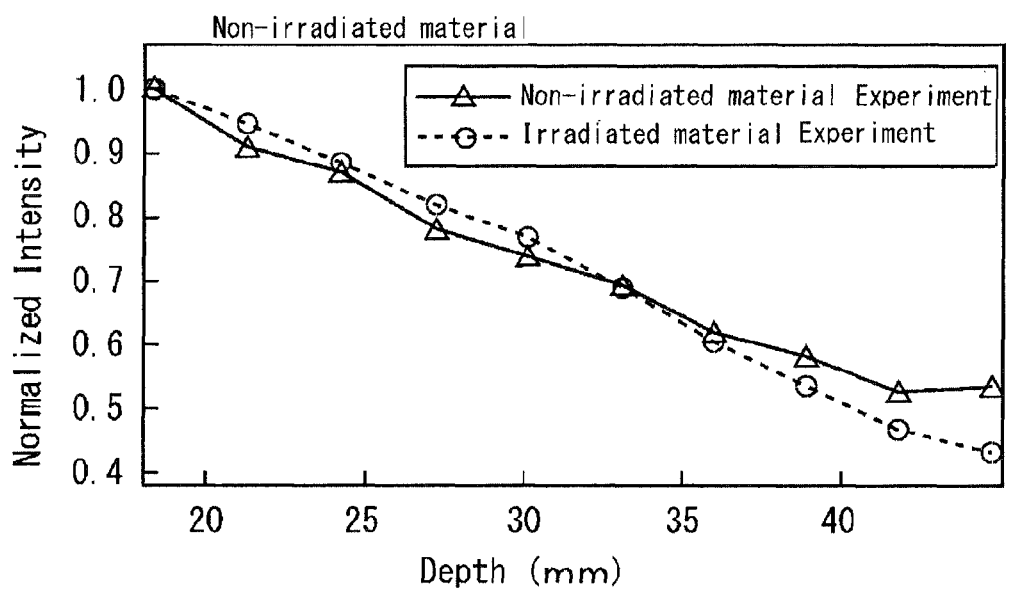
FIG. 14 is a diagram showing a result of comparison of an integrated intensity area ratio of a backscattered-wave frequency spectrum between an irradiated material and a non-irradiated material.

As seen from FIG. 14, in the irradiated material, microstructures have occurred and hence the integrated intensity area ratio of the backscattered-wave frequency spectrum has been changed from that in the non-irradiated archive material. The change is different from the change in the void swelling with a uniform distribution shown in FIG. 11 and shows a behavior close to that of swelling of 3% in the region (b) shown in FIG. 13.

Then, quantitative evaluation of the depth distribution of the microstructure change obtained in FIG. 14 was performed for the irradiated material. Specifically, results obtained by calculation using (Formulas 1 to 5) with assigning the void swelling distribution shown in Table 2 to individual depths measured from the surface are shown as theoretical values. Here, the overall length of the irradiated material is 52.2 mm. The result is shown in FIG. 15.

Figure 15:
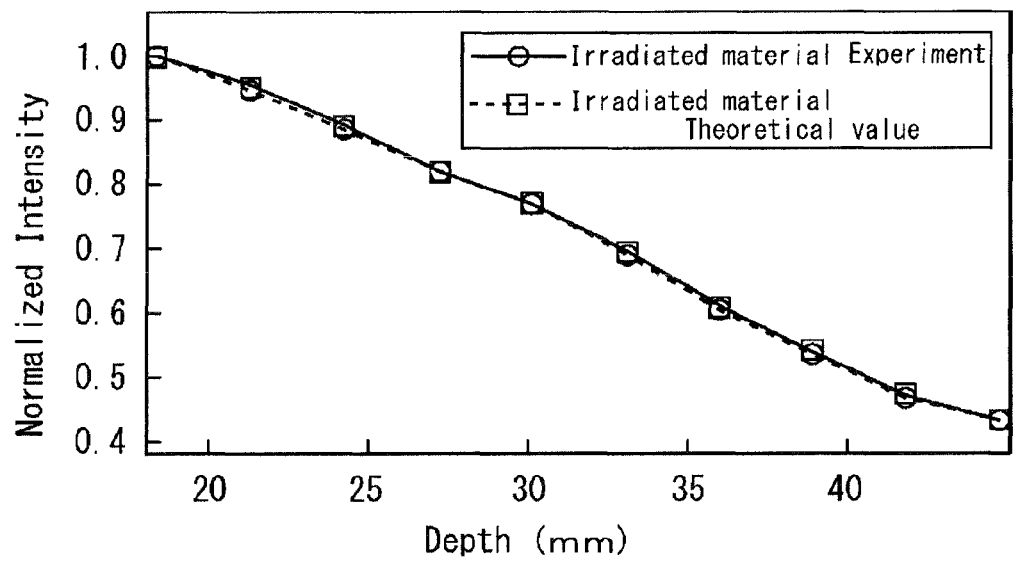
FIG. 15 is a diagram showing a result of comparison between an experimental value of an integrated intensity area ratio of a backscattered-wave frequency spectrum of an irradiated material and a theoretical calculation.

As shown in FIG. 15, satisfactory agreement is obtained between the theoretical value and the amount of void swelling obtained from the density measurement result.

TABLE 2

| | depths measured from the surface (mm) | | | | | |
|---|---|---|---|---|---|---|
| | 0-10 | 10-20 | 20-30 | 30-40 | 40-52.2 | Average |
| void swelling | 1.7 | 2.0 | 3.0 | 2.4 | 1.5 | 2.0 |
| actual density measurement result | 1.54 | 2.25 | 2.63 | 2.29 | 1.68 | 2.1 |

In the depth distribution of void swelling shown in Table 2, excellent agreement is seen between the depth distribution obtained from the density measurement result of the irradiated material and the depth distribution obtained from a void observation result by a TEM. It has been confirmed that when the method of the present invention is applied, quantitative evaluation of the depth distribution of microstructures such as voids can easily be achieved.

Here, the present inventors have confirmed that also in quantitative evaluation of the depth distribution for dislocations or precipitates having a depth distribution, the quantitative evaluation can be achieved by operation similar to the above-mentioned one.

3. Distinction in Case that Microstructures are Present Simultaneously

The following description relates to a method of distinguishing each of microstructures in a case that microstructures are present simultaneously.

(1) Assumption

It has been assumed that in the occurrence of microstructures, dislocations grow first, then carbide is precipitated, and then void swelling occurs finally.

(2) Indicators

As indicators, four indicators consisting of the sonic speed, the backscattered-wave peak frequency, and the wave heights at 7 MHz (a low frequency side) and at 13 MHz (a high frequency side) were employed.

(3) Acquisition of Ultrasonic Data

The frequency spectrum obtained when ultrasonic is projected into a material of a state without the occurrence of microstructures or of a state that each of the above-mentioned microstructures have occurred was calculated. Then, each indicator was calculated so that the relative change with reference to the value of a state without the occurrence of microstructures was acquired.

Figure 16:
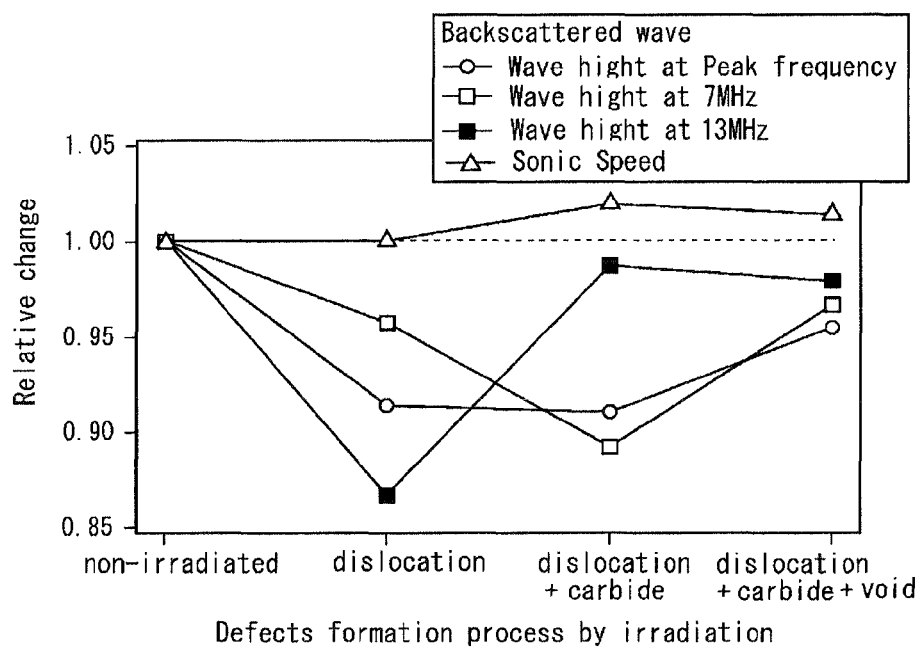
FIG. 16 is a diagram describing a distinction method for a case that microstructures occur simultaneously.

The measurement results are shown in FIG. 16. In FIG. 16, ○ indicates the wave height at the backscattered-wave peak frequency, □ indicates the wave height at 7 MHz, ■ indicates the wave height at 13 MHz, and A indicates the sonic speed.

As seen from FIG. 16, despite that the relative change in the sonic speed is not remarkably large, the relative changes in the other indicators are large. Further, depending on the state of presence of microstructures, the difference in the arrangement of each data can clearly be distinguished and hence the microstructures can be distinguished.

As such, when with focusing attention on a change in the physical property values of the crystal grain caused by the occurrence of microstructures, a large relative change can be obtained in the indicators obtained from the frequency spectrum of the backscattered wave. Then, when attention is focused on the change in these indicators, microstructures having occurred simultaneously can be distinguished.

The present invention has been described above with reference to the embodiments. However, the present invention is not limited to the above-mentioned embodiments. Various changes may be made on the above-mentioned embodiments within the scope identical or equivalent to that of the present invention.

What is claimed is:

1. A material diagnostic method of performing non-destructive diagnosis of microstructures occurring in a material using ultrasonic signals, comprising:
    performing an initial crystal grain volume calculation by
        using a first ultrasonic transducer to project a first ultrasonic signal into a first material, and to convert reflections of said first ultrasonic signal from said first material into a first ultrasonic wave form, said first material being in a state in which no microstructures has occurred,
        calculating a first attenuation coefficient for each frequency from frequency spectrums of a first bottom surface wave and a second bottom surface wave obtained by performing frequency conversion on the first ultrasonic wave form,
        acquiring a density of the first material and a sonic speed of the first ultrasonic signal, and
        calculating a volume of a crystal grain from the first attenuation coefficient, the density of the first material, and the sonic speed of the first ultrasonic signal;
    performing a diagnosis object crystal grain volume calculation by
        using a second ultrasonic transducer to project a second ultrasonic signal into a second material, which serves as a diagnosis object, and to convert reflections of said second ultrasonic signal from said second material into a second ultrasonic wave form,
        calculating a second attenuation coefficient for each frequency from frequency spectrums of a first bottom surface wave and a second bottom surface wave obtained by performing frequency conversion on the second ultrasonic wave form,
        acquiring a density of the diagnosis object and a sonic speed of the second ultrasonic signal, and
        calculating a volume of a crystal grain of the diagnosis object from the second attenuation coefficient, the density of the diagnosis object, and the sonic speed of the second ultrasonic signal; and
    performing a microstructure occurrence amount quantification by calculating an amount of volume change of the crystal grain from the individual volumes obtained during the initial crystal grain volume calculation and the diagnosis object crystal grain volume calculation, thereby quantifying an amount of occurrence of microstructures.

2. The material diagnostic method of claim 1, wherein the same ultrasonic transducer is used as the first and second ultrasonic transducers.

3. A material diagnostic method of performing non-destructive diagnosis of microstructures occurring in a material using ultrasonic signals, comprising:
    performing a first crystal grain volume calculation by
        using a first ultrasonic transducer to project a first ultrasonic waves into a first material, and to convert reflections of said first ultrasonic signal from said first material into a first ultrasonic wave form, the first material being any one of
            a material serving as a diagnosis object in an initial state;
            a same kind of material as the material serving as the diagnosis object in a state in which no microstructures have occurred; and
            the material serving as the diagnosis object in a state of having a predetermined amount of occurrence of microstructures,
        calculating a first attenuation coefficient for each frequency from frequency spectrums of a first bottom surface wave and a second bottom surface wave obtained by performing frequency conversion on the first ultrasonic wave form,
        acquiring a density of the first material and sonic speed of the first ultrasonic waves, and
        calculating a volume of a crystal grain from the first attenuation coefficient, the density of the first material, and the sonic speed of the first ultrasonic signal;
    performing a second crystal grain volume calculation by
        using a second ultrasonic transducer to project a second ultrasonic signal into the material serving as the diagnosis object, and to convert reflections of said second ultrasonic signal from said second material into a second ultrasonic wave form,
        calculating a second attenuation coefficient for each frequency from frequency spectrums of a first bottom surface wave and a second bottom surface wave obtained by performing frequency conversion on the second ultrasonic wave form, acquiring a density of the diagnosis object and a sonic speed of the second ultrasonic signal, and calculating a volume of a crystal grain of the diagnosis object from the second attenuation coefficient, the density of the diagnosis object, and the sonic speed of the second ultrasonic signal; and performing a microstructure occurrence amount quantification by calculating an amount of volume change of the crystal grain from the individual volumes obtained during the first crystal grain volume calculation and the second crystal grain volume calculation, thereby quantifying an amount of occurrence of microstructures.

4. The material diagnostic method of claim 3, wherein the same ultrasonic transducer is used as the first and second ultrasonic transducers.

5. A material diagnostic method of performing non-destructive diagnosis of microstructures occurring in a steel material caused by irradiation of radiation, using an ultrasonic signal, comprising:

performing a diagnosis object frequency spectrum calculation by using an ultrasonic transducer to project an ultrasonic signal into a material, which serves as a diagnosis object and has a predetermined amount of occurrence of microstructures, and to convert reflections of said ultrasonic signal from said material into an ultrasonic wave form, dividing a backscattered wave region of said ultrasonic wave form into intervals of predetermined width in a depth direction of the material, and calculating a frequency spectrum of the backscattered wave region of the ultrasonic waveform by using frequency conversion for each interval; and performing a microstructure depth distribution quantification by utilizing parameters corresponding to an assumed depth distribution of the microstructures to calculate a frequency spectrum of a backscattered wave for each of the intervals of predetermined width in the depth direction, and performing a comparison of the frequency spectrum of the backscattered wave calculated based on the assumed depth distribution to the frequency spectrum of the backscattered wave region of the ultrasonic wave form for each of the intervals of predetermined width in the depth direction, and determining the depth distribution of the microstructures based on the comparison so as to quantify the depth distribution of the microstructures in the material serving as the diagnosis object, wherein said microstructures, whose depth distribution is determined, are caused by irradiation on the material serving as the diagnosis object of a type of radiation which causes microstructure occurrence.

6. A material diagnostic method of performing non-destructive diagnosis of microstructures occurring in a steel material caused by irradiation of radiation, using an ultrasonic signal, comprising:

performing a diagnosis object frequency spectrum integrated-intensity area ratio calculation by using an ultrasonic transducer to project an ultrasonic signal into a material, which serves as a diagnosis object and has a predetermined amount of occurrence of microstructures, and to convert reflections of said ultrasonic signal from said material into an ultrasonic wave form, dividing a backscattered wave region of said ultrasonic wave form into intervals of predetermined width in a depth direction of the material, and calculating an integrated intensity area ratio of the frequency spectrum of the backscattered wave region of the ultrasonic wave form for each interval by using frequency conversion; and performing a microstructure depth distribution quantification by utilizing parameters corresponding to an assumed depth distribution of the microstructures to calculate a frequency spectrum of a backscattered wave for each of the intervals of predetermined width in the depth direction, and performing a comparison of an integrated intensity area ratio of the frequency spectrum of the backscattered wave calculated based on the assumed depth distribution to the integrated intensity ratio of the backscattered wave region of the ultrasonic wave form for each of the intervals of predetermined width in the depth direction, and determining the depth distribution of the microstructures based on the comparison so as to quantify the depth distribution of the microstructures in the material serving as the diagnosis object, where in said microstructures, whose depth distribution is determined, are caused by irradiation on the material serving as the diagnosis object of a type of radiation which causes microstructure occurrence.

7. A material diagnostic method of performing non-destructive diagnosis of microstructures occurring in a material using an ultrasonic signal, comprising:

performing a diagnosis object frequency spectrum calculation by using an ultrasonic transducer to project an ultrasonic signal into a material, which serves as a diagnosis object and has a predetermined dislocation density and crystal grain diameter, and to convert reflections of said ultrasonic signal from said material into an ultrasonic wave form, dividing a backscattered wave region of said ultrasonic wave form into intervals of predetermined width in a depth direction of the material, and calculating a frequency spectrum of the backscattered wave region of the ultrasonic wave form by using frequency conversion for each interval;

repeatedly performing a comparison-use frequency spectrum calculation each performance of which utilizes parameters corresponding to a different assumed by depth distribution of the microstructures to calculate a frequency spectrum for each of the intervals of predetermined width in the depth direction;

calculating, for each performance of the comparison-use frequency spectrum calculation, a difference between the frequency spectrum obtained by the comparison-use frequency spectrum calculation and the frequency spectrum obtained by the diagnosis object frequency spectrum calculation; and performing a microstructure dislocation depth distribution quantification by determining the depth distribution of the microstructures in the material from a decrease between the differences between frequency spectrums calculated for the respective performances of the comparison-use frequency spectrum calculation, thereby quantifying the dislocation depth distribution of the microstructures in the material serving as the diagnosis object.

8. A material diagnostic method of performing non-destructive diagnosis of microstructures occurring in a material using an ultrasonic signal, comprising:

performing a diagnosis object frequency spectrum integrated-intensity area ratio calculation by
using an ultrasonic transducer to project an ultrasonic signal into a material, which serves as a diagnosis object and has a predetermined occurrence of microstructures, and to convert reflections of said ultrasonic signal from said material into an ultrasonic wave form,
dividing a backscattered wave region of said ultrasonic wave form into intervals of predetermined width in a depth direction of the material, and
calculating an integrated intensity area ratio of the frequency spectrum of the backscattered wave for each interval by using frequency conversion;

repeatedly performing a comparison-use frequency spectrum integrated-intensity area ratio calculation each performance of which utilizes parameters corresponding to a different assumed depth distribution of the microstructures to calculate an integrated intensity area ratio of a frequency spectrum for each of the intervals of predetermined width in the depth direction;

calculating, for each performance of the comparison-use frequency spectrum integrated-intensity area ratio calculation, a difference between the integrated intensity area ratio of the frequency spectrum obtained by the comparison-use frequency spectrum calculation and the integrated intensity area ratio of the frequency spectrum obtained by the diagnosis object frequency spectrum calculation; and performing a microstructure dislocation depth distribution quantification by determining the depth distribution of the microstructures in the material from a decrease between the differences between integrated intensity area ratios calculated for the respective performances of the comparison-use frequency spectrum integrated-intensity area ratio calculation, thereby quantifying the dislocation depth distribution of the microstructures in the material serving as the diagnosis object.

9. A material diagnostic method of performing non-destructive diagnosis of microstructures occurring in a steel material caused by irradiation of radiation, using an ultrasonic signal, comprising distinguishing different kinds of microstructures that have occurred within a material serving as a diagnosis object, wherein the different kinds of microstructures are distinguished by using an ultrasonic transducer to project an ultrasonic signal into the material serving as the diagnosis object and using one or more indicators obtained as a result of the projecting of the ultrasonic signal, the one or more indicators being selected from: a sonic speed and an attenuation coefficient of ultrasonic signal; a frequency spectrum, a low-frequency-side wave height, and a high-frequency-side wave height of bottom surface wave; a frequency spectrum of backscattered wave; and an integrated intensity area ratio of a frequency of backscattered wave, and the different kinds of microstructures are distinguished on the basis of usage history of the material serving as the diagnosis object, and a change between material data of the diagnosis object obtained as a result of the projecting of the ultrasonic signal and standard material data acquired in advance from any one of the material serving as the diagnosis object in an initial state;

a same kind of material as the material serving as a diagnosis object in a state in which no microstructures have occurred; and the material serving as the diagnosis object in a state of having a predetermined amount of occurrence of microstructures, wherein said microstructures, the different kinds of which are distinguished, are caused by irradiation on the material serving as the diagnosis object of a type of radiation which causes microstructure occurrence.

10. A material diagnostic method of performing non-destructive diagnosis of microstructures occurring in a material using ultrasonic signals, comprising:

performing a first data acquisition by using a first ultrasonic transducer to project a first ultrasonic signal into the first material, converting reflections of said first ultrasonic waveform from said material into a first ultrasonic wave form, and calculating a crystal-grain physical property value of said first material based on the first ultrasonic wave form, the first material being any one of a material serving as a diagnosis object in an initial state, a same kind of material as the material serving as the diagnosis object in a state in which no microstructures have occurred, and the material serving as the diagnosis object in a state of having a predetermined amount of occurrence of microstructures;

performing a second data acquisition by using a second ultrasonic transducer to project a second ultrasonic signal into the material serving as the diagnosis object, converting reflections of said second ultrasonic signal from said second material into a second ultrasonic wave form, and calculating a crystal-grain physical property value of the material serving as the diagnosis object based on the second ultrasonic wave form; and performing a diagnosis of the microstructures occurring in the material serving as the diagnosis object by evaluating the second ultrasonic wave form and a change between the crystal-grain physical property value obtained by the first data acquisition and the crystal-gain physical property value obtained by the second data acquisition.

11. The material diagnostic method according to claim 10, wherein the types of microstructures diagnosed as occurring in the material serving as the diagnosis object include one or more of precipitate, void, dislocation, and phase transformation.

12. The material diagnostic method of claim 10, wherein the same ultrasonic transducer is used as the first and second ultrasonic transducers.

* * * * *